United States Patent [19]
Le Bris

[11] Patent Number: 6,015,924
[45] Date of Patent: Jan. 18, 2000

[54] PROCESS FOR THE PREPARATION OF DIACIDS FROM THE WASHING WATERS OF CYCLOHEXANE OXIDATION PRODUCTS

[75] Inventor: Louis Le Bris, Lyons, France

[73] Assignee: R.P. Fiber & Resin Intermediates, Courbevoie, France

[21] Appl. No.: 08/989,514

[22] Filed: Dec. 12, 1997

[30] Foreign Application Priority Data

Dec. 12, 1996 [FR] France .................................. 96 15524

[51] Int. Cl.⁷ .................................................. C07C 51/16
[52] U.S. Cl. .......................... 562/524; 562/512; 562/525; 562/543
[58] Field of Search .................. 562/517.4, 524, 562/512.4, 523, 525

[56] References Cited

U.S. PATENT DOCUMENTS

| | | | |
|---|---|---|---|
| 2,323,861 | 7/1943 | Zellner | 260/533 |
| 3,658,898 | 4/1972 | Lartigau | 260/537 P |
| 3,726,917 | 4/1973 | Brunie et al. | 260/533 C |
| 3,761,517 | 9/1973 | Rohl et al. | 260/531 R |
| 3,772,375 | 11/1973 | Brunie et al. | 260/533 C |
| 3,997,601 | 12/1976 | Langley | 260/531 R |
| 4,014,903 | 3/1977 | Moore | 260/345.9 |
| 4,227,021 | 10/1980 | Grosskinsky et al. | 516/513 |

FOREIGN PATENT DOCUMENTS

| | | |
|---|---|---|
| 1334673 | 12/1963 | France . |
| 2061956 | 6/1971 | France . |
| 2219144 | 9/1974 | France . |

*Primary Examiner*—Paul J. Killos
*Assistant Examiner*—Taylor V. Oh
*Attorney, Agent, or Firm*—Burns, Doane, Swecker & Mathis, L.L.P.

[57] ABSTRACT

The present invention relates to a process for the preparation of diacids or mixtures of diacids from aqueous solutions derived from the washing of cyclohexane oxidation products. More specifically, the present invention provides a process for the preparation of aliphatic diacids from washing waters derived from a process for the oxidation of cyclohexane and containing peroxides, the process of the invention comprising successively:

(a) at least partially deperoxidizing said washing waters by subjecting them to catalytic hydrogenation at a temperature of between about 0° C. and about 100° C., in the presence of at least one platinum group metal;

(b) oxidizing with nitric acid the products contained in the washing waters after deperoxidation.

21 Claims, No Drawings

PROCESS FOR THE PREPARATION OF DIACIDS FROM THE WASHING WATERS OF CYCLOHEXANE OXIDATION PRODUCTS

BACKGROUND OF THE INVENTION

1. Technical Field of the Invention

The present invention relates to a process for the preparation of diacids or mixtures of diacids from aqueous solutions derived from the washing of cyclohexane oxidation products.

2. Description of the Prior Art

It is known to oxidize cyclohexane, essentially into cyclohexanone and cyclohexanol, with gas mixtures containing molecular oxygen, in the presence or absence of a catalyst.

Thus, during the air oxidation of cyclohexane, in the liquid phase, without catalysts, cyclohexanol and cyclohexanone are primarily obtained. It is also known in this type of process to eliminate, before distilling these compounds, at least some of the side products formed during the oxidation reaction. This elimination is usually carried out by washing with water and/or using alkaline aqueous solutions, either at the end of the oxidation reaction or during or between the various phases of the oxidation.

The products contained in these washing waters are especially peroxides, in particular acid peroxides, mainly 6-hydroperoxyhexanoic acid and polymers derived therefrom.

These washing waters may also contain hydroxycaproic acid in free or esterified form, adipic acid, glutaric acid and/or succinic acid, as well as 5-formylvaleric acid.

Various processes for upgrading these washing waters, in particular into adipic acid, have been proposed.

Thus, patent FR-A-2,061,956 describes a process for the preparation of adipic acid by oxidation, using molecular oxygen under pressure, of 6-hydroperoxyhexanoic acid in aqueous solution. Patent FR-A-1,594,895 and its first certificate of addition FR-A-2,054,701 describe a process for the preparation of adipic acid by oxidation with nitric acid, optionally in the presence of nitrogen peroxide, of the 6-hydroperoxyhexanoic acid contained in the aqueous washing solution.

Processes for the hydrogenation of the acids contained in the washing waters into corresponding alcohols have also been described.

Thus, U.S. Pat. No. 3,985,814 describes a process for the hydrogenation of the acids contained in washing waters into corresponding alcohols, in the presence of platinum deposited on carbon black, under a pressure of 300 bar and at 265° C. This process appears to be relatively effective, since the degree of conversion of the acids into alcohols is about 95%, but the hydrogenation conditions are very harsh, which makes the process too expensive for industrial use. Moreover, this process, by definition, converts the acids into alcohols, which thus does not provide the desired upgrading into dicarboxylic acids.

A process based on the same reactions, carried out under similar temperature and pressure conditions but using a catalyst chosen from ruthenium, rhenium, cobalt, nickel and chromium, is described in German patent DE-A-1,957,396.

Lastly, French patent FR-1,585,375 describes a process for the preparation of ε-hydroxyhexanoic acid by catalytic hydrogenation of 6-hydroperoxyhexanoic acid, which must be extracted and separated from the washing waters beforehand, using an organic solvent.

Although, admittedly, these known processes make it possible to obtain diacids, in particular adipic acid, or their alcohol intermediates which can optionally be oxidized, they nevertheless all have at least one of the following drawbacks:

(i) their industrial implementation is too expensive because of the conditions under which the reactions must be carried out;

(ii) the adipic acid thus obtained is of insufficient purity to be used directly as an intermediate in the synthesis of polyamide fibers, thus necessitating a subsequent excessive purification treatment;

(iii) these processes process only part of the washing waters, not all of them.

SUMMARY OF THE INVENTION

The aim of the present invention is thus, in particular, to provide a process for the preparation of aliphatic diacids, in particular adipic acid and mixtures of adipic acid, glutaric acid and succinic acid, from washing waters derived from a process for the oxidation of cyclohexane and comprising peroxides, the said process for the preparation of diacids not having the drawbacks mentioned above.

The process of the invention makes it possible, in particular, to obtain adipic acid in a purity which is sufficient to be used as an intermediate in the synthesis of polyamide-6,6, in particular for textile fibers, as well as high-quality mixtures of adipic acid, glutaric acid and succinic acid, while at the same time being a process which is inexpensive to implement industrially and allowing all of the compounds contained in the washing waters to be processed.

Another aim of the present invention is to provide a process in which the peroxidized compounds contained in the washing waters mentioned above are decomposed selectively and completely under moderate temperature and pressure conditions, whereas their elimination in the prior processes leads to the formation of impurities which are found in the diacids obtained and in particular in adipic acid.

More specifically, the present invention provides a process for the preparation of aliphatic diacids from washing waters derived from a process for the oxidation of cyclohexane and containing peroxides, the present process comprising successively:

(a) at least partially deperoxidizing said washing waters by subjecting them to catalytic hydrogenation at a temperature of between about 0° C. and about 100° C., in the presence of at least one platinum group metal;

(b) oxidizing with nitric acid the products obtained in the washing waters after the deperoxidation step.

DETAILED DESCRIPTION OF THE BEST MODE AND SPECIFIC/PREFERRED EMBODIMENTS OF THE INVENTION

In the present text, the term "platinum group metal" is understood to include platinum, palladium, rhodium, ruthenium, iridium and osmium.

It is necessary to first carry out the deperoxidation in step (a) before the nitric oxidation in step (b), otherwise impurities would be formed during the nitric oxidation, which would be found in the diacids at the end of the process.

The catalytic hydrogenation used for the deperoxidation in step (a) is preferably carried out at a temperature of from about 20° C. to about 80° C.

Between steps (a) and (b), the hydrogenate obtained in (a) can advantageously be concentrated, by elimination of some of the water contained therein.

The washing waters to which the process of the invention is applied can originate from any process of oxidation of cyclohexane with air, oxygen-enriched air or oxygen-depleted air, provided that the said washing waters contain peroxides. They can be derived more particularly from the process described in patent FR-1,580,206.

In these cyclohexane oxidation processes, the oxidates are washed according to any conventional technique of liquid-phase washing, it being possible for the operation to be carried out continuously or non-continuously.

The washing with water can thus be carried out in the liquid phase at a temperature of between about 5° C. and about 100° C., under autogenous pressure or under a pressure created by an inert gas such as nitrogen. The weight of water used generally represents from about 0.01 to about 1 times the weight of the oxidate to be washed and preferably from about 0.05 to about 0.5 times this weight.

The platinum group metal hydrogenation catalyst for step (a) is preferably platinum, palladium or rhodium. It can be deposited on a support such as silica, alumina, carbon or an alumino silicate. The catalyst is preferably in the form of a powder or in the form of granules. The hydrogenation reaction is carried out non-continuously, for example in an autoclave, or preferably continuously, for example in a column with a supported catalytic bed, or alternatively, semi-continuously.

The hydrogenation step (a) can be carried out under a hydrogen pressure equal to atmospheric pressure, but the reaction kinetics are then slow and there is a risk of side reactions occurring due to a lack of hydrogen.

For this reason, it is preferred to work under a hydrogen pressure of from 5 to 50 bar at temperature, and even more preferably from 10 to 30 bar. The process could be performed under a pressure above 50 bar, but this would not give rise to any specific advantages, since the hydrogenation reaction kinetics are sufficiently high in the zones defined above, especially in the preferred zone, and in particular when the catalyst used is palladium.

When the hydrogenation reaction is carried out continuously, a hydrogenation reactor with supported catalytic bed is used, fed with an aqueous solution preferably containing not more than about 3% peroxides on a weight-for-weight basis, and even more preferably not more than about 2% peroxides.

Step (b) comprising oxidation with nitric acid is carried out using an aqueous nitric acid solution having a weight titer of between about 40% and about 65% and preferably between about 55% and about 60%.

A molar excess of nitric acid relative to the alcohol functions to be oxidized is generally used. In practice, from about 4 to about 8 mol of nitric acid are used per mole of alcohol function contained in the solution for processing.

The oxidation can be carried out in the presence or absence of a catalyst, such as a vanadium-based catalyst, optionally combined with copper, cobalt, titanium, nickel, chromium, molybdenum or cerium.

Among these catalysts, vanadic acid and ammonium and sodium metavanadates are preferred. In practice, this catalyst is mixed with the aqueous nitric acid solution used in a proportion of from about 0.02 mol to about 0.2 mol of metal per liter of acid solution, irrespective of its concentration.

Unexpectedly, it has been demonstrated that the oxidation reaction can be carried out in the absence of a metal catalyst, as mentioned above, without the yield of adipic acid obtained being affected. In addition, aliphatic diacids free of metals can thus be obtained at the end of the process, which is particularly advantageous for some of their subsequent uses.

In order to avoid uncontrolled runaway of the oxidation reaction, the deperoxidized solution is gradually introduced into the aqueous nitric acid solution, working at a relatively low temperature, for example between about 15° C. and about 50° C.

One of the advantages of the process of the invention, arising essentially from the fact that the mixture subjected to the oxidation with nitric acid contains virtually no peroxides, is precisely that it is possible to carry out this oxidation at a temperature of from about 15° C. to about 50° C. and preferably between about 30° C. and about 45° C.

These temperature ranges are not critical. However, if the temperature is above about 50° C., for example about 90° C., the process can nevertheless be carried out, but the yield of adipic acid lowers. If the temperature is below about 15° C., precipitation of adipic acid may occur.

At the end of the oxidation step, it may be prudent to increase the temperature temporarily in order to complete the reaction and to eliminate certain undesirable side products such as, for example, oxalic acid. The temperature at which this finishing operation can be carried out is between about 50° C. and about 100° C. and preferably between about 70° C. and about 90° C., and its duration can range from a few minutes to several hours, for example between about 15 minutes and about 2 hours.

The adipic acid can be separated from the reaction mixture obtained after the oxidation reaction according to the usual processes such as, for example, crystallization consisting of cooling the mixture and filtering of the adipic acid precipitated.

The adipic acid thus separated is then recrystallized according to the usual techniques in order to obtain an adipic acid of purity which is sufficient to be used in the manufacture of polyamide-6,6, in particular for textiles.

The filtrate obtained after precipitation of the adipic acid can be evaporated to dryness in order to lead to a molten mixture of diacids, essentially a mixture of succinic acid, glutaric acid and adipic acid, advantageously free of metals, if the step (b) oxidation has been carried out according to a preferred variant without a catalyst. By way of example, the filtrate can, more specifically, be treated according to the technique described in patent FR-A-2,111,003.

A particularly advantageous variant for the processing of the filtrate makes it possible to prepare mixtures of the diacids mentioned above of excellent quality, in particular as regards their color and their purity. This variant comprises in heating the crude mixture containing the succinic acid, glutaric acid and adipic acid, in the molten state, for a period of a few minutes to several hours. The temperature at which the heating is carried out can range, for example, from about 140° C. to about 220° C. The duration is generally between about 30 minutes and about 15 hours, but these amounts are not considered critical. The above heat treatment is followed by distillation of the mixture of diacids as described in patent FR-A-2,111,003. The mixtures thus obtained comprise generally, for more than about 90% of their weight, of succinic acid, glutaric acid and adipic acid, the relative proportions of these diacids varying in particular according to the temperature at which the reaction mixture obtained after the oxidation step is cooled in order to precipitate the adipic acid.

These mixtures of diacids can be used in particular in the form of their esters, essentially their alkyl esters, such as the methyl, ethyl, propyl, butyl, pentyl and hexyl esters, as solvents in many different applications. They can also act as plasticizers in the form of their heavier esters, such as the octyl esters. They can also act as acidifiers in the textile industry or the leather industry.

The examples which follow further illustrate the present invention. These examples are intended only as illustrative and in nowise limitative.

EXAMPLE 1

The starting solution is an aqueous solution from the washing of a cyclohexane solution containing hydroperoxides, derived from an oxidation reaction of cyclohexane with oxygen-depleted air, in the liquid phase and without a catalyst, the said oxidation reaction having been followed by concentration of the final reaction mixture.

The aqueous solution has a content of organic materials (in particular 6-hydroxyhexanoic acid, adipic acid, succinic acid, glutaric acid, adipic semialdehyde, esters and peroxides) of 19.5% on a weight-for-weight basis, including 9.7% peroxides.

Step (a) of Hydrogenation 2500 g of this solution are subjected to hydrogenation, by supplying them continuously at a rate of 2 liters/hour, at 25° C. and under a pressure of 10 bar of hydrogen, into a stirred autoclave in the presence of 1% by weight, relative to the total weight of the said solution, of a powdered catalyst comprising 10% by weight of Pd metal deposited on charcoal.

At the end of the supply state, the autoclave is degassed and 2805 g of reaction mixture comprising 15.4% of heavy organic materials (432 g) are removed.

2525 g of this hydrogenate are concentrated in order to obtain 735 g of concentrate with a titer of 52.5% by weight of heavy organic materials.

Step (b) of Oxidation 669.5 g of the above deperoxidized concentrate are employed in the nitric oxidation step.

The oxidation is carried out in the absence of catalyst, in apparatus comprising a stirred reactor.

2010 g of nitric acid at 58% on a weight-for-weight-basis are introduced into the reactor, after which the 669.5 g of concentrate are run in over 2 h, while maintaining the temperature of the reaction mixture at 40° C. The temperature is then raised to 90° C. and this temperature is maintained for 1 h. The reaction mixture is subsequently cooled to room temperature and the apparatus is degassed. The adipic acid precipitate (161.4 g after drying) is filtered off.

After recrystallization of this adipic acid, a product of very high quality is obtained, which is suitable for the manufacture of polyamide-6,6.

The filtrate is concentrated to dryness in order to give a mixture comprising:

52.5 g of adipic acid
83.8 g of glutaric acid
40.2 g of succinic acid.

This mixture is heated for 10 h at 150° C. and is then distilled using a film evaporator.

The distilled mixture obtained is in the form of flakes that are white to very pale yellow in color to the eye (coloration, according to the Gardner Index, of 6).

EXAMPLE 2

The process is performed as in step (a) of Example 1. An aqueous washing solution having a weight content of organic materials of 13.85%, 10.1% of which consist of peroxides, is hydrogenated.

Three successive operations are performed by injecting in total 6000 g of aqueous solution and hydrogenating at 25° C. under 10 bar of hydrogen, in the presence of 1% by weight, relative to the weight of the solution subjected to the hydrogenation, of catalyst consisting of Pt deposited to a proportion of 5% on carbon black. Each hydrogenation lasts one hour.

The hydrogenate is removed, and gives a titer of 13.2% by weight of heavy organic materials (792 g).

5781 g of this hydrogenate are concentrated in order to obtain 1386 g of concentrate containing 755 g of heavy organic materials.

Nitric oxidation of 410 g of this concentrate is carried out as described in Example 1, at 40° C., in 2002 g of 58% nitric acid.

After cooling and filtration of the precipitate formed, 82.6 g of adipic acid (dry weight) are obtained.

EXAMPLE 3

The starting solution is an aqueous solution from the washing of a cyclohexane solution containing hydroperoxides, derived from an oxidation reaction of cyclohexane with oxygen-depleted air, in the liquid phase and without a catalyst, the said oxidation reaction having been followed by concentration of the final reaction mixture.

The aqueous solution has a content of organic materials (in particular 6-hydroxyhexanoic acid, adipic acid, succinic acid, glutaric acid, adipic semialdehyde, esters and peroxides) of 15.1% on a weight-for-weight basis, including 10.3% peroxides.

This solution is hydrogenated continuously in a column reactor with an irrigated catalytic bed. The catalyst consists of graphite granules containing 0.5% by weight of Pd.

The solution is prediluted using pre-hydrogenated aqueous solutions in order to have a peroxide concentration at the top of the hydrogenation reactor of 1.57%. The hydrogen pressure is 20 bar and the temperature is 25° C.

There are no longer any peroxides at the foot of the reactor.

The operations of concentration and nitric oxidation are then carried out on a part of the hydrogenate, as indicated in Example 1. Adipic acid is obtained which, after recrystallization, is a product of very high quality, which is suitable for the manufacture of polyamide-6,6.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of aliphatic diacids from washing waters derived from a process for the oxidation of cyclohexane and containing peroxides, which comprises successively:

(a) at least partially deperoxidizing said washing waters by subjecting them to catalytic hydrogenation at a temperature of between about 0° C. and about 100° C., in the presence of at least one platinum group metal; and (b) oxidizing with nitric acid the products obtained in the washing waters after the deperoxidation step.

2. A process according to claim 1, wherein the platinum group metal is platinum, palladium, rhodium, ruthenium, iridium or osmium.

3. A process according to claim 1, wherein the catalytic hydrogenation used for the deperoxidation in step (a) is carried out at a temperature of from about 20° C. to about 80° C. and under a hydrogen pressure of from about 5 to about 50 bar at temperature.

4. A process according to claim 3, wherein the catalytic hydrogenation is carried out under a hydrogen pressure of from about 10 to about 30 bar.

5. A process according to claim 2, wherein the catalytic hydrogenation used for the deperoxidation in step (a) is carried out at a temperature of from about 20° C. to about 80° C. and under a hydrogen pressure of from about 5 to about 50 bar at temperature.

6. A process according to claim 5, wherein the catalytic hydrogenation is carried out under a hydrogen pressure of from about 10 to about 30 bar.

7. A process according to claim 1, wherein, between steps (a) and (b), the hydrogenate obtained in step (a) is concentrated by elimination of some of the water contained therein.

8. A process according to claim 1, wherein the washing waters used in step (a) originate from a process of oxidation of cyclohexane with air, oxygen-enriched air or oxygen-depleted air, in which the oxidates are washed by liquid-phase washing.

9. A process according to claim 8, wherein washing of the oxidates is carried out continuously.

10. A process according to claim 8, wherein washing of the oxidates is carried out non-continuously.

11. A process according to claim 8, wherein the washing with water is carried out in the liquid phase at a temperature of between about 5° C. and about 100° C., under the autogenous pressure or under a pressure created by an inert gas, the weight of water used representing from about 0.01 to about 1 times the weight of the oxidate to be washed.

12. A process according to claim 11, wherein the weight of water used represents from about 0.05 to about 0.5 times the weight of the oxidate to be washed.

13. A process according to claim 1, wherein step (a) is carried out continuously in a hydrogenation reactor with a catalytic bed, said reactor being supplied with an aqueous solution containing not more than about 3% peroxides, on a weight-for-weight basis.

14. A process according to claim 13, wherein said reactor is supplied with an aqueous solution containing not more than about 2% peroxides, on a weight-for-weight basis.

15. A process according to claim 1, wherein the step (b) oxidation with nitric acid is carried out using an aqueous nitric acid solution having a weight titer of between about 40% and about 65%.

16. A process according to claim 15, wherein the aqueous nitric acid solution has a weight titer of between about 55% and about 60%.

17. A process according to claim 1, wherein step (b) oxidation with nitric acid is carried out using a molar excess of nitric acid relative to the alcohol functions to be oxidized.

18. A process according to claim 17, wherein the step (b) oxidation with nitric acid is carried out using from about 4 to about 8 mol of nitric acid per mole of alcohol function contained in the solution for processing.

19. A process according to claim 1, wherein the step (b) oxidation is carried out in the presence of a catalyst.

20. A process according to claim 19, wherein the step (b) oxidation is carried out in the presence of a vanadium-based catalyst, optionally combined with copper, cobalt, titanium, nickel, chromium, molybdenum or cerium.

21. A process according to claim 1, wherein the step (b) oxidation is carried out in the absence of a catalyst.

* * * * *